US011577001B2

(12) United States Patent
Deister

(10) Patent No.: US 11,577,001 B2
(45) Date of Patent: Feb. 14, 2023

(54) AMNION TISSUE GRAFTS AND METHODS OF PREPARING AND USING SAME

(71) Applicant: AxoGen Corporation, Alachua, FL (US)

(72) Inventor: Curt Deister, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 688 days.

(21) Appl. No.: 16/346,607

(22) PCT Filed: Nov. 2, 2017

(86) PCT No.: PCT/US2017/059700
§ 371 (c)(1),
(2) Date: May 1, 2019

(87) PCT Pub. No.: WO2018/085527
PCT Pub. Date: May 11, 2018

(65) Prior Publication Data
US 2019/0282732 A1    Sep. 19, 2019

Related U.S. Application Data

(60) Provisional application No. 62/416,528, filed on Nov. 2, 2016.

(51) Int. Cl.
*A61L 27/38* (2006.01)
*A61L 27/36* (2006.01)
*A01N 1/00* (2006.01)
*A61K 35/12* (2015.01)

(52) U.S. Cl.
CPC ............ *A61L 27/3804* (2013.01); *A01N 1/00* (2013.01); *A61K 35/12* (2013.01); *A61L 27/3604* (2013.01); *A61L 27/3687* (2013.01); *A61L 27/3691* (2013.01); *A61L 27/3895* (2013.01)

(58) Field of Classification Search
None
See application file for complete search history.

(56) References Cited

U.S. PATENT DOCUMENTS

| 4,801,299 A * | 1/1989 | Brendel | A61F 2/10 623/7 |
|---|---|---|---|
| 8,105,634 B2 | 1/2012 | Liu et al. | |
| 8,420,126 B2 | 4/2013 | Tseng et al. | |
| 8,460,716 B2 | 6/2013 | Daniel | |
| 8,932,641 B2 | 1/2015 | Nikaido et al. | |
| 2003/0187515 A1 | 10/2003 | Hariri et al. | |
| 2005/0032209 A1 * | 2/2005 | Messina | A61P 19/04 435/372 |
| 2005/0260176 A1 * | 11/2005 | Ayares | A61L 27/3604 424/93.7 |
| 2008/0069895 A1 | 3/2008 | Liu et al. | |
| 2009/0208551 A1 * | 8/2009 | Kim | A61L 27/365 424/430 |
| 2012/0078378 A1 * | 3/2012 | Daniel | A61K 35/19 623/23.72 |
| 2013/0156863 A1 * | 6/2013 | Tseng | A61K 35/50 424/583 |
| 2013/0204393 A1 | 8/2013 | Samaniego | |
| 2013/0344163 A1 * | 12/2013 | Tseng | A61K 35/51 424/583 |
| 2014/0341871 A1 * | 11/2014 | Morris | A61K 35/36 435/325 |
| 2014/0342014 A1 * | 11/2014 | Tseng | A61P 27/02 424/572 |

FOREIGN PATENT DOCUMENTS

| CN | 2905071 Y | 5/2007 |
|---|---|---|
| CN | 105521523 A | 4/2016 |
| JP | 2008-22715 A | 2/2008 |
| JP | 2014-138590 A | 7/2014 |
| KR | 20050083804 A | 8/2005 |
| KR | 20080032212 A | 4/2008 |
| WO | WO 2007/009062 A5 | 1/2007 |
| WO | 2007/029676 A1 | 3/2007 |
| WO | 2012112441 A1 | 8/2012 |
| WO | WO 2017/132503 A1 | 8/2017 |

OTHER PUBLICATIONS

PBS, PBS recipe, Cold Spring Harbor Protocols, 2015 (Year: 2015).*
Setra, Vacuum pressure, Webpage, Oct. 2015 (Year: 2015).*
Tween, Tween Trademark Database Entry, 2022 (Year: 2022).*
Supplementary European search report in European Application No. 17866477.7, dated May 26, 2020 (15 pages).
International Search Report and Written Opinion received in International Patent Application No. PCT/US2017/059700, dated May 24, 2018, pp. 1-14.

* cited by examiner

*Primary Examiner* — Blaine Lankford
(74) *Attorney, Agent, or Firm* — Bookoff McAndrews, PLLC

(57) ABSTRACT

The invention provides method for preparing amnion tissue grafts, as well as the grafts themselves. In specific embodiments, the tissue graft comprises a single layer of dried amnion from an umbilical cord.

16 Claims, 1 Drawing Sheet

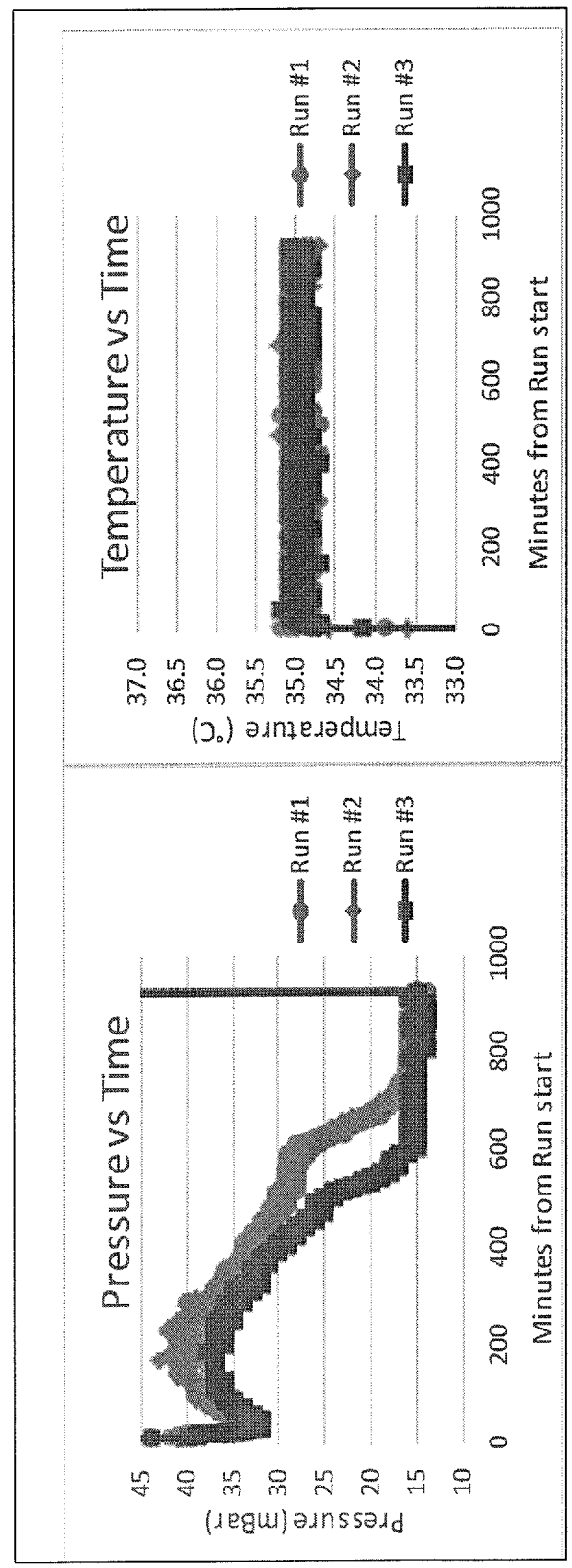

AMNION TISSUE GRAFTS AND METHODS OF PREPARING AND USING SAME

CROSS-REFERENCE TO RELATED APPLICATIONS

This application is a U.S. National Stage of International Patent Application No. PCT/US2017/059700, filed 02 Nov. 2017, which claims priority to U.S. Provisional Application Ser. No. 62/416,528, filed on 02 Nov. 2016, the disclosure of which is incorporated herein by reference in their entirety.

BACKGROUND

Tissue grafts are useful for various types of surgical procedures and wound treatments. The tissue used in graft procedures can be collected from humans or from animal specimens. Alternatively, graft tissue can be manufactured artificially. One source of human tissue, which has been utilized for decades in surgical procedures, is the placental membrane.

The placenta is an organ that develops during pregnancy to surround the fetus and connect it to the uterine wall. This temporary organ allows for transport of gases and nutrients to the fetus, while also providing other metabolic and endocrine functions. The placental membrane consists of two layers of tissue: amnion, the innermost layer surrounding the developing fetus, and chorion, an outer layer surrounding the amnion and fetus. The amniotic membrane forms an avascular, fluid-filled sac around the fetus, which holds and protects the fetus during development.

In addition to the amniotic sac, another major placental component is the umbilical cord. This cord-like structure, which attaches a fetus to the placenta, provides nutrition and support to the developing embryo. A human umbilical cord is typically about 50-60 cm long and 2 cm in diameter. It consists of blood vessels surrounded by a smooth, protective mesenchymal material known as Wharton's jelly, all of which is contained in a tube formed of amnion.

Amnion tissue grafts are generally used to assist in tissue regeneration and aid in wound healing. Known clinical procedures or applications for amnion grafts include, but are not limited to, ocular reconstruction, burn treatment, gum tissue replacement, and general wound care.

Amnion tissue provides unique grafting characteristics when used for surgical procedures. Some amnion tissue grafts have the ability to self-adhere or to be fixed in place by, for example, fibrin glue or suturing.

While using fresh membrane is typically ideal, the limited timeframe available for storage of fresh tissue makes such use difficult. Thus, processing methods are needed to facilitate preserving and storing tissue until it is needed for surgical applications. The main goal of tissue processing and preservation is to retain the beneficial components of fresh tissue while achieving a shelf life long enough to last until surgery. When prepared properly, amnion tissue grafts can be stored for extended periods of time.

BRIEF SUMMARY OF THE INVENTION

The subject invention provides methods for preparing amnion tissue grafts, as well as the grafts themselves. In specific embodiments, the tissue graft comprises a single membrane of dried amnion from an umbilical cord.

In one embodiment, the method comprises the steps of:
a) making a longitudinal cut in the amnion of an umbilical cord to expose the contents of the lumen of the umbilical cord;
b) removing blood vessels and Wharton's jelly from the lumen of the umbilical cord to produce a debrided amnion;
c) optionally, incubating the debrided amnion in a holding solution;
d) washing the debrided and, if performed, incubated, amnion in the holding solution;
e) rinsing the washed amnion one or more times in a rinsing solution; and
f) drying the rinsed amnion.

In another embodiment, a partially debrided amnion is obtained and further processed by washing, rinsing, and drying and optionally, holding before the washing step.

BRIEF DESCRIPTION OF THE DRAWINGS

FIG. 1 shows Pressure and Temperature charts from drying runs.

DETAILED DISCLOSURE OF THE INVENTION

Amniotic membrane forms the inner lining of the placenta and umbilical cord during fetal development. The amniotic membrane has three distinct layers; a single layer of epithelial cells, a thick basement membrane and a non-vascular stromal layer. It contains no HLA antigens or MHC molecules and is therefore an immunologically privileged material. The primary structural component of amniotic membrane is extracellular matrix consisting of collagens and proteins such as fibronectin, proteoglycans, laminin and glycosaminoglycans. Other molecules found in amniotic membrane include growth factors, metalloproteinases and tissue inhibitors of metalloproteinases, which together with the extracellular matrix components may play a role in wound healing and cellular ingrowth.

The subject invention provides methods for preparing amnion tissue grafts, as well as the grafts themselves. In specific embodiments, the tissue graft comprises a dried single layer amnion from an umbilical cord.

In one embodiment, the method comprises the steps of:
a) making a longitudinal cut in the amnion of an umbilical cord to expose the contents of the lumen of the umbilical cord;
b) removing blood vessels and Wharton's jelly from the lumen of the umbilical cord to produce a debrided amnion;
c) optionally, incubating the debrided amnion in a holding solution;
d) washing the debrided and, if performed, incubated, amnion in the holding solution;
e) rinsing the washed amnion one or more times in a rinsing solution; and
f) drying the rinsed amnion.

In another embodiment, a partially debrided amnion is obtained and further processed by washing, rinsing, and drying and optionally, holding before the washing step.

Selected Definitions

"Subject" refers to an animal, such as a mammal, for example a human. The methods described herein can be useful for isolating amnion from both humans and non-human animals. In some embodiments, the subject is a mammal. The invention can be used in a subject selected from non-limiting examples of a human, non-human primate, rat, mouse, pig, horse, cattle, dog or cat.

"Amnion" as used herein refers to amniotic membrane of an umbilical cord.

"Umbilical cord" refers to a cordlike structure containing blood vessels that attaches a fetus to the placenta during gestation. An umbilical cord comprises a wall of amnion enclosing a lumen comprising, among other substances, Wharton's jelly and blood vessels.

Producing the Amnion Tissue Graft

In one embodiment, a longitudinal cut in the amnion is made along the full length of an umbilical cord. The umbilical cord can then be laid out flat in approximately rectangular shape with amnion at the bottom and the contents of the lumen over the amnion. The luminal contents of the umbilical cord can be removed from the amnion in a process referred to as "debriding" the amnion. The process of debriding comprises separating the contents of the umbilical cord from the amnion using appropriate tools, for example, surgical tools such as forceps, scissors, and the like.

The purpose of the debriding step is to remove all or substantially all of the luminal contents. Wharton's jelly is an amorphous gel-like mass; it may not be possible, or desireable, to remove 100% of the Wharton's jelly. Accordingly, for the purposes of the invention, "removing Wharton's jelly from the luminal contents of the umbilical cord" means that more than about 50%, 70%, 80%, 90%, 95%, and even more than 99%, of the Wharton's jelly from the lumen of an umbilical cord is separated from the amnion. Therefore, some Wharton's jelly may be left in the debrided amnion.

In one embodiment, an amount of Wharton's jelly remains that substantially or completely fills valleys between ridges that would otherwise exist in the amnion tissue.

In one embodiment, the debridement step is performed in a rinsing solution. In one embodiment, the rinsing solution is phosphate buffered saline comprising:
1) NaCl: 7 to 11 g/L; preferably, 8-10 g/L; more preferably, about 9 g/L;
2) Anhydrous $Na_2HPO_4$: 0.2 to 1.5 g/L; preferably, about 0.5 to 1 g/L; more preferably, about 0.8 g/L; and
3) $KH_2PO_4$: 0.1 to 0.2 g/L; preferably, about 0.15 g/L.
At pH: 7 to 8.8; preferably about 7.4.

In a particular embodiment, the rinsing solution comprises about 9 g/L NaCl, about 0.8 g/L anhydrous $Na_2HPO_4$, about 0.14 g/L $KH_2PO_4$, at a pH of about 7.4.

In certain embodiments, the rinsing solution does not contain calcium or magnesium.

In one embodiment, the debrided amnion is stored in a holding solution for a holding period. The holding period can be about two to five hours, particularly, about two, three, four or five hours. The holding step can be performed at a temperature of between 20° C. to 30° C., preferably, at about 25° C.

In one embodiment, the holding solution comprises:
1) Tween®-20 (Polyethylene glycol sorbitan monolaurate): 0.4% to 0.6% (v/v); preferably about 0.5% (v/v);
2) An antimicrobial compound: For example, polyaminopropyl biguanide (also called, polyhexamethylene biguanide hydrochloride or PHMB) at 0.04% to 0.06% (w/v), preferably about 0.05% (w/v). In another embodiment, the antimicrobial compound is chlorhexidine gluconate at a concentration of, for example 0.01% to 1.5% and, more preferably, from 0.03% to 0.08%. Additional antimicrobial compounds, for example, antibiotics or antifungal agents and their appropriate concentrations are known to a person of ordinary skill in the art and such embodiments are within the purview of the invention;
3) NaCl: 7 to 10 g/L; preferably, 8-9 g/L; more preferably, about 9 g/L; and
4) An appropriate buffer, at pH 6.0 to 8.0, preferably, 6.5 to 7.0; preferably, about 6.6 to 6.8; and more preferably, 6.7±0.1. An example of a buffer that can be used in the holding solution is Bis-Tris Propane buffer, 8 to 12 mM; preferably, 9 to 11 mM; more preferably, about 10 mM. Additional examples of buffers include MES, Bis-Tris, ADA, ACES, PIPES, MOPSO, BES, MOPS, TES, HEPES, DIPSO, MOBS, TAPSO, HEPPSO, POPSO, EPPS (HEPPS), Tricine, Gly-Gly, Bicine, HEPBS, TAPS, AMPD, TABS, AMPSO, CHES, CAPSO, AMP, CAPS, and CAPS.

In a particular embodiment, the holding solution comprises about 0.5% (v/v) Tween®-20 (Polyethylene glycol sorbitan monolaurate); about 9 g/L NaCl; about 0.05% (w/v) PHMB; and about 10 mM Bis-Tris Propane buffer at pH of 6.7±0.1.

In one embodiment, the debrided amnion, with or without the holding step, is stored at about 4° C. for about 10 to 15 hours before a washing step. The step of storing debrided amnion at 4° C. can be performed in the holding solution.

In another embodiment, the debrided amnion, either with or without the holding step, is washed in a washing step. Preferably, the washing step comprises agitating the debrided amnion in the holding solution.

Agitation during the washing step can be performed, for example, on a shaker for about two to five hours, particularly, for about two, three, four, or five hours. Agitation can be performed at about 50 to 300 rotations per minute (RPM), preferably at about 100 to 200 RPM, more preferably at about 125 to 175 RPM, even more preferably, at about 150 RPM.

In one embodiment, a debrided amnion is stored in a holding solution in the holding step and the washing step is performed in the same holding solution by transferring the amnion to a shaker.

After the washing step, the washed amnion is rinsed in a rinsing step. The rinsing step is performed in the rinsing solution, described above. In a particular embodiment, the rinsing solution used in the rinsing step comprises about 9 g/L NaCl, about 0.8 g/L anhydrous $Na_2HPO_4$, and about 0.14 g/L $KH_2PO_4$, at a pH of about 7.4.

In one embodiment, the step of rinsing is performed three to five times in a rinsing solution. Each rinsing step can be performed for about 5 to 30 minutes; preferably, for about 10 to 25 minutes; and even more preferably, for about 15 minutes.

The rinsing step can be performed on a shaker at about 50 to 300 RPM, preferably at about 100 to 200 RPM, more preferably at about 125 to 175 RPM, even more preferably, at about 150 RPM.

The step of rinsing is designed to remove components of the washing solution from the graft as well as remaining blood or debris from the debriding step.

In one embodiment, the rinsed amnion is dried. The step of drying can be performed for about 5 to 25 hours, preferably, for about 10 to 20 hours, and even more preferably, for about 15 hours. In one embodiment, drying is performed at a pressure lower than the atmospheric pressure, for example, at a pressure of between about 15 mBar to 60 mBar. In a typical drying process under reduced pressure, a pressure of about 40 to 60 mBar, preferably, between 45 to 55 mBar, more preferably, about 50 mBar is used at the beginning of the drying step. The pressure can change over time during the step of drying as shown in FIG. 1. The pressure at the end of the drying process of about 12 to 16 hours can be, for example, about 10 to 15 mBar.

In a specific embodiment, the step of drying is performed for about 15 hours at a temperature of between 30° C. and 40° C. and under initial pressure of between about 50 mBar, which reduces to a pressure of about 15 mBar towards the end of the drying step.

A further embodiment of the invention provides a method for preparing a dried amnion membrane from umbilical cord, the method comprising the steps of:

a) obtaining a partially-debrided amnion;

b) removing, blood vessels and Wharton's jelly to produce a debrided amnion;

c) optionally, incubating the debrided amnion in a holding solution;

d) washing the debrided and, if performed, incubated, amnion in the holding solution;

e) rinsing the washed amnion one or more times in a rinsing solution; and f) drying the washed amnion.

The partially-debrided amnion can be obtained in a frozen state, in which case, the frozen partially-debrided amnion is thawed before further processing. Thawing can be performed over about 6 to 20 hours, preferably over about 8 to 15 hours, and more preferably, over about 10 to 12 hours. Thawing can be performed at a temperature of between 20° C. to 30° C., preferably, between 22° C. to 28° C., even more preferably, at about 24° C. to 25° C.

The steps of removing the blood vessels and the Wharton's jelly to produce a debrided amnion, incubating the debrided amnion in a holding solution, washing the debrided and if performed, incubated, amnion in the holding solution, rinsing the washed amnion one or more times in the rinsing solution, and drying the rinsed amnion are described above and such description is applicable to the embodiment of the invention where a partially debrided amnion is the starting materials.

Amnion Tissue Grafts

The umbilical cord/amnion tissue grafts produced according to the subject invention may be, for example, ½ cm to 4 cm wide and, for example, 2 to 6 cm long.

In one embodiment the graft is provided with an indicium of which side is from the outside of the umbilical cord and which side is from the inside of the umbilical cord. In one embodiment, the indicium is a tab provided at a specified corner of the graft. As used herein, reference to a "tab" means a protrusion out from the edge of the graft. The protrusion may be, for example, in the shape of a rectangle, square or triangle. In one embodiment, to place the graft endothelial side up, the tab is in the upper left corner. When used in practice, the tab also helps a user to grasp the tissue graft with a tool, for example, a forceps. Tabs are also useful in repositioning the tissue graft at a surgical site, for example, a user can maneuver the tissue graft at the surgical site by grasping the tissue graft with a tool, for example, a forceps, and repositioning the tissue graft as desired.

The tissue grafts prepared according to the subject invention are processed such as they have less than 20% water content. Preferably, the water content is about 12% to about 18%. In preferred embodiments, the water content is 15% or less.

The graft preferably contains no blood vessels, or chorion tissue. That is, the graft consists, or consists essentially of, amnion tissue, typically including some Wharton's jelly.

When dried (e.g., after processing), the tissue graft has a thickness of about 150 µm to 250 µm, preferably about 175 µm to 225 µm. As noted above, the tissue grafts comprise an amount of Wharton's Jelly that makes the surface smooth (e.g., few, if any, ridges). Preferably, the graft has uniform thickness, varying by less than 20%, 15%, 10%, 5%, 2%, or even 1% across its surface.

The tissue graft can be sterilized with e-beam irradiation of about, for example, less than 25 KGy and, preferably, about 15-19 KGy.

The tissue grafts comprise no live cells, glycerol or ice crystals.

In one embodiment, the graft is treated with, for example, ascorbic acid to improve its whiteness.

In one embodiment, the graft is coated, or infused, with an antimicrobial composition that persists with the graft so as to reduce and/or prevent infections once the graft is implanted. The antimicrobial composition may be, for example, polyhexanide (polyhexamethylene biguanide, PHMB) or chlorhexidine gluconate (CHG) (or other salt thereof) in an amount such that microbes are exposed to about 0.01% to about 1.0% CHG and preferably about 0.02% to about 0.08%. Most preferably to concentration of CHG is about 0.03% to 0.05%. The graft may comprise other substances including, but not limited to, growth factors, anti-inflammatory agents, and stem cells. The amnion tissue grafts produced according to the methods described herein show similar levels of bioactive compounds as present in the amnion used to produce the tissue graft. Such bioactive compounds include interleukins, tissue inhibitors of metalloproteinases, epidermal growth factor, fibroblast growth factor, platelet derived growth factor, vascular endothelial growth factor, and transforming growth factor present before and after processing. These bioactive compounds facilitate healing when the tissue grafts of the invention are placed are used in surgical procedures.

Advantageously, the amnion tissue grafts of the subject invention have sufficient strength to be sutured. The suture may be, for example, a size 7-0, 8-0, or even 9-0 USP size or smaller suture, which advantageously does not tear through the graft.

The tissue graft may be packaged inside a first foil package that is sterile inside and out and placed within the sterile inside of a second package.

Use of the Amnion Tissue Graft

The amnion tissue grafts can be used, for example, to assist in tissue regeneration and aid in wound healing. Exemplary clinical procedures or applications for the subject amnion grafts include, but are not limited to, tendon repair, dural defects, intra-abominable adhesions, peritoneal reconstructions, genital reconstruction, ocular reconstruction, burn treatment, gum tissue replacement, nerve repair, promote healing at surgical sites, and general acute and chronic wound care.

The tissue graft may be placed directly at the surgical site or rehydrated prior to placement. If rehydration is desired, room temperature sterile saline or sterile Lactated Ringer's solution (LRS) can be used for rehydration.

When placed at a surgical site, either as dry or after rehydration, the tissue grafts of the invention drape and conform to the tissue or organ on which they are placed. Thus, the tissue grafts can self-adhere to the tissue or organ on which they are placed. Adherence of the tissue grafts to a tissue or an organ can be facilitated by suturing the tissue graft to the site. The self-adherence property of the tissue grafts of the invention can be enhanced by designing the tissue grafts to have rounded corners. Rounding of the corners facilitate placement of the tissue grafts at a site in the body because the rounded corners conform to the target site more easily than sharp corners, for example, right angled corners. Although the tissue graft conforms and adheres to the tissue or organ, the tissue grafts have sufficient strength to be repositioned by a user, for example, a surgeon, without breaking or disintegrating.

When implanted the tissue graft remains in place for 8, 10, 12, 16 or more weeks. Advantageously, the tissue grafts of the subject invention can be used to help prevent or reduce scar tissue by favorably modifying the host immune response via, for example, a barrier function at the site of the injury.

As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Bench-Top Execution of a Human Umbilical Cord Membrane Processing

This Example provides a procedure for extraction of materials from the tissue and retention of process residuals in the tissue.

The aqueous processing time used in this Example was intended to maximize the potential for extracting materials, such as growth factors or components of the extracellular matrix, from the tissue before testing. Using milder processing conditions less extraction occurs.

Additionally, the use of tissue that was prepared after recovery and before freezing by having the cord cut open and bulk tissue removed from the stromal face, maximizes the surface area for diffusion of materials out of the tissue during the recovery process and the thawing before debridement. Reducing times and volumes for the rinse series between the detergent wash and the drying process increases the potential for retention of processing agents and so maximizes the risk of affecting biocompatibility.

Equipment:
1. Shaker incubator
2. Biosafety cabinets
3. Vacuum drying oven
4. Vacuum Sealer
5. Balance
6. Push gauge
7. Refrigerator Debridement Tissue was obtained in the frozen state with significant debridement already conducted. This "pre-debridement" removed bulk tissue and variable amounts of the blood vessels. Thawing the frozen tissue was conducted at ambient temperature (~24° C.) overnight. Average thaw time was 15:21 hr with a range of 14:34 to 17:03 hrs.

Debridement involved cutting open and removing any remaining blood vessels with forceps. Bulk tissue (principally Wharton's Jelly) was then removed with curved iris scissors until all tissue above the plane of the tissue that could be gripped firmly between Adson forceps (e.g., tissue "ridges" that can be gripped without also gripping the membrane itself) was removed.

The average cord length was 44.5 cm (32 to 68 cm range). Debridement produced a wet tissue membrane that was about 1300±300 microns thick with a range of 510 to 1900 microns.

The unprocessed tissue membranes were collected immediately after debridement and after measurements were made, the membranes were stored in sterile conical tubes in a refrigerator until the drying step.

Processed samples were also collected immediately after debridement and then measured but were then processed with the remainder of the cord before drying.

Processing

Table 1 below shows the durations and set-points of the process run in this Example. n=3 for the three processing runs except where noted when the step references individual donors.

TABLE 1

| Processing parameters | | | |
|---|---|---|---|
| | Avg. value | Min | Max |
| Pre-rinse (Step 1b) | | | |
| Duration (n = 12) | 1:47 | 1:01 | 2:48 |
| Volume of Sol. F (L) | 2 +/− 0.05 | NA | NA |
| Temperature (° C.) (set-point) | 28 | NA | NA |
| RPM's (set-point) | 150 | NA | NA |

TABLE 1-continued

Processing parameters

|  | Avg. value | Min | Max |
|---|---|---|---|
| Prost-Debridement hold (Step 2) | | | |
| Duration (hr) | 3:00 | 3:00 | 3:02 |
| Volume of Sol. H (L) | 2 +/− 0.05 | NA | NA |
| Room Temperature, No agitation | Yes | NA | NA |
| Wash (Step 3) | | | |

Solution was not changed between the holding and the washing step, i.e., the solution used in the holding step is used while shaking in the washing step.

|  | Avg. value | Min | Max |
|---|---|---|---|
| Duration (hr) | 3:33 | 3:30 | 3:38 |
| Temperature (° C.) (set-point) | 30.0 | NA | NA |
| RPM's (set-point) | 150 | NA | NA |
| Rinse #1 (Step 4) | | | |
| Duration (min) | 10 | 10 | 11 |
| Volume of Sol F (L) | 1.5 +/−0.05 | NA | NA |
| Temperature (° C.) (set-point) | 22.0 | NA | NA |
| RPM's (set-point) | 130 | NA | NA |
| Rinse #2 (Step 5) | | | |
| Duration (min) | 10 | 10 | 10 |
| Volume of Sol F (L) | 1.5 +/− 0.05 | NA | NA |
| Temperature (° C.) (set-point) | 22.0 | NA | NA |
| RPM's (set-point) | 130 | NA | NA |
| Rinse #3 (Step 6) | | | |
| Duration (min) | 10 | 10 | 10 |
| Volume of Sol. F (L) | 1.5 +/− 0.05 | NA | NA |
| Temperature (° C.) (set-point) | 22.0 | NA | NA |
| RPM's (set-point) | 130 | NA | NA |
| Rinse #4 (Step 7) | | | |
| Duration (min) | 11 | 10 | 13 |
| Volume of Sol. F (L) | 1.5 +/− 0.05 | NA | NA |
| Temperature (° C.) (set-point) | 22.0 | NA | NA |
| RPM's (set-point) | 130 | NA | NA |
| Drying (Step 8) | | | |
| Duration, hr (start to door open) | 15.4 | 15.4 | 15.5 |

Solution F is rinsing solution and Solution H is holding solution.

Drying

Drying was performed as described below.

TABLE 2

Drying program used (from Table 2 of protocol)

| Drying step | Temperature (° C.) (Start)/(Finish) | Pressure (mBar) (Start)/(Finish) | Time (hr) |
|---|---|---|---|
| Step 1 (start step) | Ambient/35 | Ambient/35 | NA. till conditions met |
| Step 2 | 35/35 | 35/15 | 1 min (note pressure will not be reached) |
| Step 3 | 35/35 | 15/15 | 15 |
| Total time | ~15 | hrs | |
| Time weighted average temperature | 35 | | ° C. (approximate, timed steps only) |
| Time weighted average pressure | 15 | | mBar (approximate, timed steps only) |

The drying procedure dried the tissue at about 30° C. to 40° C., preferably, about 33° C. to 37° C., even more preferably about, 34° C. to 36° C., and particularly, about 35° C. The drying step is performed in a medium vacuum. The final vacuum pressure (absolute) can be about 10 to 20 mBar, preferably, about 12 to 18 mBar, even more preferably, about 14 to 16 mBar, and particularly, about 15 mBar. However, the vacuum pressure at any time during the drying process is related to the water content of the tissue.

The drying time was 15-16 hours (note that the actual time may vary as the 1st step continues until pressure and temperature are met and will vary based on initial conditions). For example, in one embodiment, the required temperature and pressure are reached within about 1 to 10 minutes, in about 2 to 5 minutes, or in about 2 to 3 minutes.

The pressure and temperature profiles of three development runs are shown in FIG. 1.

In all three runs, the chamber was at approximately 15 mBar by 730 minutes after the start of the run. Condensation was observed on the inside of the front window of the chamber in approximately the same timeframe as the pressure increase observed at about 50 minutes into the run. A "shoulder" is observed in the pressure plot between 30 and 25 mBar which might represent the end of primary drying (i.e. removal of water not bound to other molecules). The chamber temperature varied less than 0.5° C. from the set-point through the run after the set-point was reached.

To reduce the possibility of absorbing moisture from the atmosphere, the drying assemblies still in the drying bag were placed in poly bags and sealed with a zip tie until used (if sizing and packaging was not started immediately). The processed and unprocessed samples showed an average loss of mass on drying of 95% (Table 3).

TABLE 3

Wet and dry weights of tissue samples

| | Run #1 | | | | Run #2 | | | | Run #3 | | | |
|---|---|---|---|---|---|---|---|---|---|---|---|---|
| | Lot #1 | Lot #2 | Lot #3 | Lot #4 | Lot #1 | Lot #2 | Lot #3 | Lot #4 | Lot #1 | Lot #2 | Lot #3 | Lot #4 |
| Wet weight, g (unprocessed sample) | 1.121 | 1.81 | 1.434 | 1.522 | 1.394 | 1.479 | 1.71 | 1.673 | 1.392 | 2.399 | 1.433 | 1.662 |
| Dry weight, g (unprocessed sample) | 0.077 | 0.09 | 0.075 | 0.078 | 0.054 | 0.077 | 0.099 | 0.091 | 0.079 | 0.112 | 0.082 | 0.081 |

TABLE 3-continued

Wet and dry weights of tissue samples

| | Run #1 | | | | Run #2 | | | | Run #3 | | | |
|---|---|---|---|---|---|---|---|---|---|---|---|---|
| | Lot #1 | Lot #2 | Lot #3 | Lot #4 | Lot #1 | Lot #2 | Lot #3 | Lot #4 | Lot #1 | Lot #2 | Lot #3 | Lot #4 |
| Wet weight, g (processed sample) | 1.047 | 1.399 | 1.547 | 1.445 | 1.285 | 1.92 | 2.288 | 1.719 | 0.85 | 1.401 | 1.574 | 1.855 |
| Dry weight, g (processed sample) | 0.053 | 0.069 | 0.058 | 0.163 | 0.058 | 0.099 | 0.089 | 0.091 | 0.045 | 0.06 | 0.084 | 0.069 |
| % decrease in Unprocessed weight | 93.1% | 95.0% | 94.8% | 94.9% | 96.1% | 94.8% | 94.2% | 94.6% | 94.3% | 95.3% | 94.3% | 95.1% |
| % decrease in Processed weight | 94.9% | 95.1% | 96.3% | 88.7% | 95.5% | 94.8% | 96.1% | 94.7% | 94.7% | 95.7% | 94.7% | 96.3% |
| Avg % decrease in Unprocessed weight | | | 94.7% | SD | 0.7% | | Avg % decrease in weight, all samples | | | 94.8% | SD | 1.5% |
| Avg % decrease in Processed weight | | | 94.8% | SD | 2.0% | | | | | | | |

Weights from scale result in significant figures.
Percentages are shown at 3 significant figures.

Appearance and Final Sizing

Samples were manually sized using a scalpel and ruler. Lots with samples intended for bioburden testing were sized first using an autoclaved cutting board. Subsequent Lots within each Run were sized using a disposable cutting board with a pre-printed cm scale grid. This disposable cutting board was not steam sterilizable, but was cleaned with 70% isopropyl alcohol and air-dried prior to use.

Tissue Thicknesses

Accounting for the significant digits of the measurement, wet tissue after debridement was 1300±300 microns in thickness and dry tissue was 200±60 microns in thickness. The observed range for wet tissue (24 samples; 64 measurements) was 510 to 1900 microns. The observed range for dry tissue (24 samples; 72 measurements) was 50 to 300 microns.

TABLE 5

Tissue thicknesses

| | Run #1 | | | | Run #2 | | | | Run #3 | | | |
|---|---|---|---|---|---|---|---|---|---|---|---|---|
| | Lot #1 | Lot #2 | Lot #3 | Lot #4 | Lot #1 | Lot #2 | Lot #3 | Lot #4 | Lot #1 | Lot #2 | Lot #3 | Lot #4 |
| Wet thickness, Thous (unprocessed sample) | 42 | 51 | 42 | 75 | 45 | 36 | 35 | 52 | 48 | 28 | 51 | 64 |
| | 43 | 53 | 62 | 63 | 60 | 32 | 33 | 26 | 64 | 60 | 46 | 55 |
| | NA | NA | NA | NA | 56 | 47 | 64 | 57 | 22 | 57 | 54 | 46 |
| Dry thickness, Thous (unprocessed sample) | 9 | 5 | 5 | 10 | 3 | 4 | 7 | 10 | 7 | 10 | 7 | 6 |
| | 9 | 4 | 6 | 5 | 3 | 4 | 9 | 2 | 5 | 6 | 6 | 6 |
| | 12 | 8 | 4 | 9 | 3 | 5 | 4 | 9 | 5 | 11 | 6 | 4 |
| Wet thickness, Thous (processed sample) | 47 | 50 | 55 | 63 | 46 | 35 | 63 | 38 | 20 | 59 | 52 | 53 |
| | 50 | 50 | 60 | 54 | 56 | 44 | 73 | 63 | 44 | 43 | 66 | 48 |
| | NA | NA | NA | NA | 55 | 42 | 54 | 64 | 49 | 37 | 53 | 40 |
| Dry thickness, Thous (processed sample) | 8 | 7 | 7 | 10 | 5 | 8 | 4 | 9 | 6 | 4 | 5 | 7 |
| | 6 | 12 | 5 | 7 | 7 | 7 | 5 | 11 | 5 | 4 | 6 | 5 |
| | 6 | 12 | 12 | 6 | 6 | 8 | 7 | 11 | 5 | 7 | 6 | 4 |
| Average Wet thickness, Unprocessed sample in Thousandths of inch: | | | | | 49 | SD | 13 | | in microns | 1245 | SD | 323 |
| Average Wet thickness, Processed sample in Thousandths of inch: | | | | | 51 | SD | 11 | | in microns | 1291 | SD | 271 |
| Overall Average Wet thickness in Thousandths of inch: | | | | | 50 | SD | 12 | | in microns | 1268 | SD | 297 |
| Average Dry thickness, Unprocessed sample in Thousandths of inch: | | | | | 6 | SD | 3 | | in microns | 161 | SD | 65 |

TABLE 5-continued

Tissue thicknesses

|  | Run #1 | | | | Run #2 | | | | Run #3 | | | Lot #4 |
|---|---|---|---|---|---|---|---|---|---|---|---|---|
|  | Lot #1 | Lot #2 | Lot #3 | Lot #4 | Lot #1 | Lot #2 | Lot #3 | Lot #4 | Lot #1 | Lot #2 | Lot #3 |  |
| Average Dry thickness, Processed sample in Thousandths of inch: |  |  |  | 7 | SD |  | 2 |  | in microns | 176 | SD | 60 |
| Overall Average Dry thickness in Thousandths of inch: |  |  |  | 7 | SD |  | 2 |  | in microns | 169 | SD | 63 |

Gauge used, an analogue dial gauge, showed either 2 or 3 significant figures as read.
This table shows the micron conversion to one micron.
SD: Standard Deviation, Thous: Thousandth of an inch

TABLE 6

Aqueous Process Conditions

| | Tested (this protocol) | | | | | Alternative Process | | | | |
|---|---|---|---|---|---|---|---|---|---|---|
| | | Agitation | | | | | Agitation | | | |
| Process Step | Time | setpoint (rpm) | Temperature setpoint (° C.) | Solution | Volume (L) | Time | setpoint (rpm) | Temperature (° C.) | Solution | Volume (L) |
| Step 1, Debridement | Perform as rapidly as possible in Biosafety Cabinet | | | storage solution (0.9% saline) | minimal volume to keep tissue wet | Perform as rapidly as possible in Biosafety Cabinet | | | storage solution (0.9% saline) | NA, minimal volume to keep tissue wet |
| Step 1b, Post-debridement incubation (each donor enters at a different time) | 1:47 hr (1:01-2:48) | 150 | 28 | F | 2 ± 0.05 | Step not in alternative process | | | | |
| Step 2, Post-debridement hold | 3:00 hr (3:00-3:02) | 0 | ambient (held in hood) | H | 2 ± 0.05 | 0-2.5 hr | 0 | ambient | H | 1.95 ± 0.05 |
| Step 3, Process Wash | 3:33 hr (3:30-3:38) | 150 | 30 | H | No solution change | 1-1.5 hr | 140 ± 5 | 26 ± 2 | H | No solution change |
| Step 4, Process Rinse #1 | 10 min (10-11) | 130 | 22 | F | 1.5 ± 0.05 | 15-40 min | 140 ± 5 | 26 ± 2 | F | 1.95 ± 0.05 |
| Step 5, Process Rinse #2 | 10 min (10-10) | 130 | 22 | F | 1.5 ± 0.05 | 15-40 min | 140 ± 5 | 26 ± 2 | F | 1.95 ± 0.05 |
| Step 6, Process Rinse #3 | 10 min (10-10) | 130 | 22 | F | 1.5 ± 0.05 | 15-40 min | 140 ± 5 | 26 ± 2 | F | 1.95 ± 0.05 |
| Step 7, Process Rinse #4 | 11 min (10-13) | 130 | 22 | F | 1.5 ± 0.05 | 15-40 min | 140 ± 5 | 26 ± 2 | F | 1.95 ± 0.05 |
| Total aqueous process time | 7:15 hr (7:12-7:21) not including time of changes | | | | | 2:00 to 6:40 not including time of changes | | | | |

TABLE 7

Drying Process Conditions

| | This Example | | | Alternative Process | | |
|---|---|---|---|---|---|---|
| Drying step | Temperature (° C.) (Start)/(Finish) | Pressure (mBar) (Start)/(Finish) | Time (hr) | Temperature (° C.) (Start)/(Finish) | Pressure (mBar) (Start)/(Finish) | Time (hr) |
| Step 1 (start step) | Ambient/35 | Ambient/35 | Till conditions met | Ambient/35 | Ambient/35 | Till conditions met |
| Step 2 | 35/35 | 35/15 | 1 min (note pressure will not be reached) | 35/35 | 35/15 | 1 min (note pressure will not be reached) |

TABLE 7-continued

Drying Process Conditions

| | This Example | | | Alternative Process | | |
|---|---|---|---|---|---|---|
| Drying step | Temperature (° C.) (Start)/(Finish) | Pressure (mBar) (Start)/(Finish) | Time (hr) | Temperature (° C.) (Start)/(Finish) | Pressure (mBar) (Start)/(Finish) | Time (hr) |
| Step 3 | 35/35 | 15/15 | 15 | 35/35 | 15/15 | 16 |
| Step 4 | | NA | | Shut off heating element (set to 20° C.) and vent chamber with nitrogen then shut down system. This holds the tissue in an inert environment (~1 atm of nitrogen and approximately ambient temperature) until the chamber is opened. | | |
| Total time (start to door open or nitrogen purge) | | 15.4 hr (15.4-15.5) | | ~16.5 hrs | | |

CONCLUSIONS

Tissue thawing was conducted at ambient temperature (~24°) overnight, 14-18 hrs. Debridement resulted in a wet membrane of about 1.3 mm thickness, which was reduced after drying to about 0.2 mm. The weight loss on drying observed was about 95% for all samples. Table 6 summarizes the aqueous processing conditions tested and potential conditions for an alternative process. The potential alternative process conditions are selected to be overall milder processing conditions for the tissue (principally less total contact time) while providing greater potential to remove residual processing agents (increased time, agitation, and temperature in Steps 3-7).

Table 7 summarizes the drying processing conditions tested and potential conditions for an alternative process. The potential alternative process conditions are selected ensure that the drying observed is at least as robust as that observed in this protocol.

Alternative solutions to the nitrogen purge as a terminal hold step are possible, such as shutting the heating element off and maintaining vacuum. The samples made under this protocol are appropriate for characterization testing.

I claim:

1. A method for preparing a dried amnion tissue graft from an umbilical cord, the method comprising the steps of:
    making a longitudinal cut in an amnion of the umbilical cord that has a lumen in order to expose contents of the lumen;
    removing, from the contents of the lumen, blood vessels and more than 50%, but not all, of Wharton's jelly to produce a debrided amnion;
    incubating the debrided amnion in a holding solution before washing the debrided amnion in the holding solution, and wherein the remaining Wharton's jelly substantially or completely fills valleys between ridges on a surface of the amnion, wherein the dried amnion tissue graft from the umbilical cord has a thickness in a range of 175 um to 225 um, and wherein the thickness varies by less than 1% across a surface of the dried amnion tissue graft;
    rinsing the washed amnion one or more times in a rinsing solution; and
    drying the rinsed amnion.

2. The method of claim 1, wherein the holding solution comprises:
    polyethylene glycol sorbitan monolaurate at 0.4% to 0.6% (v/v),
    an antimicrobial compound,
    NaCl at 7 to 10 g/L, and
    a buffer at pH of 6.5 to 7.0.

3. The method of claim 1, wherein the step of washing is conducted for two to five hours and comprises agitation performed at 100 to 200 rotations per minute.

4. The method of claim 1, wherein the rinsing solution has a pH of 7 to 8.8 and comprises:
    NaCl at 7 to 10 g/L,
    $Na_2HPO_4$ at 0.5 to 1.5 g/L, and
    $KH_2PO_4$ at 0.1 to 0.2 g/L.

5. The method of claim 1, wherein the step of rinsing is performed for three to five times in the rinsing solution and each rinsing step is performed at 100 rotations per minute to 200 rotations per minute.

6. The method of claim 1, wherein the debrided amnion is stored at 4° C. before the washing step.

7. The method of claim 1, wherein the step of drying is performed at a temperature of 30° C. to 40° C.

8. A method for obtaining a dried amnion membrane from an umbilical cord, the method comprising the steps of:
    removing blood vessels and more than 50%, but not all, of Wharton's jelly from an amnion obtained from the umbilical cord to produce a debrided amnion;
    washing the debrided amnion in a holding solution;
    rinsing the washed amnion one or more times in a rinsing solution; and
    drying the rinsed amnion,
    wherein the dried amnion membrane from the umbilical cord has a thickness in a range of 175 μm and 225 μm, wherein the thickness varies by less than 20% across a surface of the dried amnion membrane, and wherein the Wharton's jelly that remains in the dried amnion membrane substantially or completely fills valleys between ridges on the surface of the dried amnion membrane.

9. The method of claim 8, wherein the obtained amnion is a partially-debrided amnion in a frozen state and the method further comprises thawing the frozen partially-debrided amnion, and
    wherein the thickness varies by less than 1% across a surface of the dried amnion tissue graft.

10. The method of claim 8, further comprising:
    incubating the debrided amnion in the holding solution before washing the debrided amnion in the holding solution.

11. The method of claim 8, wherein the holding solution comprises:
polyethylene glycol sorbitan monolaurate at 0.4% to 0.6% (v/v), an antimicrobial compound,
NaCl at 7 to 10 g/L, and
a buffer at pH of 6.5 to 7.0.

12. The method of claim 8, wherein the step of washing is conducted for two to five hours and comprises agitation performed at 100 rotations per minute to 200 rotations per minute.

13. The method of claim 8, wherein the rinsing solution has a pH of 7 to 8.8 and comprises:
NaCl at 7 to 10 g/L,
$Na_2HPO_4$ at 0.5 to 1.5 g/L, and
$KH_2PO_4$ at 0.1 to 0.2 g/L.

14. The method of claim 8, wherein the step of rinsing is performed for three to five times in a rinsing solution and wherein each rinsing step is performed at 100 rotations per minute to 200 rotations per minute.

15. The method of claim 8, wherein the debrided amnion is stored at 4° C. before the washing step.

16. The method of claim 8, wherein the step of drying is performed at a temperature of between about 30° C. to 40° C.

* * * * *